United States Patent [19]
Dudney

[11] Patent Number: 5,733,777
[45] Date of Patent: Mar. 31, 1998

[54] PACKAGING SYSTEM FOR EXTENDED SHELF LIFE OF MICROBIAL SYSTEM

[76] Inventor: Ralph A. Dudney, 10803 W. Hidden Lake La., Richmond, Tex. 77469-9722

[21] Appl. No.: 659,343

[22] Filed: Jun. 6, 1996

[51] Int. Cl.⁶ ............................................. C12M 1/24
[52] U.S. Cl. ........................ 435/304.1; 435/307.1; 435/309.1; 435/810
[58] Field of Search ................... 435/287.4, 287.6, 435/287.9, 288.1, 288.2, 288.3–288.5, 303.2, 304.1, 304.2, 305.1–305.4, 307.1, 810, 260, 309.1, 309.2; 604/82, 87, 92, 416

[56] References Cited

U.S. PATENT DOCUMENTS

| | | | |
|---|---|---|---|
| 2,619,448 | 11/1952 | Larsen | 435/304.2 |
| 2,687,130 | 8/1954 | Cohen | 604/92 |
| 3,360,440 | 12/1967 | Haab et al. | 435/304.2 |
| 3,415,361 | 12/1968 | Adams, Jr. et al. | 435/288.3 |
| 4,009,285 | 2/1977 | Spooner | 435/304.2 |
| 4,392,492 | 7/1983 | Pick | 604/82 |
| 4,589,835 | 5/1986 | St. Amand | 156/198 |
| 5,155,039 | 10/1992 | Chrisope et al. | 435/307.1 |

*Primary Examiner*—William H. Beisner
*Attorney, Agent, or Firm*—William J. Beard

[57] ABSTRACT

A packaging system is disclosed for use in storing and conveniently and sterilely activating a useful microbial system in a culture medium. The system includes a conveniently sized bottle of sterile culture broth in a bottle capped with a conventional screw on cap. A second storage cap is provided having an elastomeric o-ring seal at its top and an impermeable sealing disc across the o-ring seal. The space inside the o-ring seal between the sealing disc and the top of the cap contains the lyophilized microorganism inoculant. Removal of the sealing disc and replacement of the first cap with the second cap on the bottle of culture broth then, upon inversion, inoculates the culture broth.

6 Claims, 1 Drawing Sheet

PACKAGING SYSTEM FOR EXTENDED SHELF LIFE OF MICROBIAL SYSTEM

FIELD OF THE INVENTION

The present invention relates to packaging systems for live microbial or bacterial systems. More particularly, the present system relates to packaging for such live microbial systems which is useful to greatly extend the usable shelf life of the product.

BACKGROUND OF THE INVENTION

A copending U.S. patent application Ser. No. 08/488,820, filed Jun. 9, 1995, now issued as U.S. Pat. No. 5,616,318 discloses the use of the bacterial strain *Xenorhabdus Nematophilus* IM-1 or ATCC-19061-1 for the control of the pest Imported Red Fire Ant, *Solenopsis Invicta*. Cultures of the bacteria used in testing its efficacy for this purpose were grown in a sterile liquid broth and, using slow rotary shaking, incubated from 24–72 hours therein. The resulting liquid culture can be diluted from 50:1 to 20:1 and applied directly to mounds of the pest, being very effective in eliminating them.

Unfortunately for marketing purposes of such a bacterial system the shelf life of such a concentrated liquid culture can be, at most, only a few weeks or months.

In any closed, liquid culture system, the microorganisms inevitably proceed through their growth curve from lag, log growth, maximum stationary, and log death phases. Known ways to stop the microbes in a closed culture from proceeding through the growth curve is to inhibit their metabolic processes at the desired stage. This may be accomplished by physical processes such as freezing, drying, or lyophilizing the cells, or by the addition of chemical metabolic inhibitors. Although these processes do accomplish the stated goal, they also possess certain inherent drawbacks. First, if the desired product is a viable microbial culture, any manipulation may open the culture to possible contamination by microbes in the environment. Secondly, the inhibiting processes and their reversal may cause varying degrees of death or loss of desired biological activity, such as infectivity. Thirdly, the processes and their reversal may require technical expertise, specialized equipment or supplies. Fourth, reversal of chemical inhibition may require addition of other chemicals or dilution beyond the desired concentration. Finally, all of the procedures are likely to raise the cost of the final product and increase the chance of failure. All of these problems may be included the term, "the shelf life problem." If a microbial culture must be young to mature, but not old, to be efficacious, it should be used at the appropriate window of time. This is the case with Xenorhabdus on fire ants. Old or senescent cultures have many dead or dormant cells which may be incapable of infecting and killing the fire ants. Thus, if a culture in the correct, active growth stage, sets on a shelf for a while, the cells become old and die or changes to another phase of the strain which is much less effective.

BRIEF DESCRIPTION OF THE INVENTION

The shelf life problem does impact the use of viable, metabolically active microorganisms by the individual consumer. The present invention discloses a packaging system whereby the retailer may store a capped container of sterile growth media and a separate sterile replaceable cap containing the inoculum and packed in sterile sealed plastic or foil. The inoculum may be lyophilized (freeze dried) or in other forms such as a sterile sealed plastic pipette that maintain the desired microbe in a viable, but dormant state. These forms may change, such as by providing the inoculant in a sealed plastic pipette in an agar gel, depending upon the microorganism that is intended to be grown in the medium. The medium can also vary, depending upon the microorganism to be cultured. With sterile culture medium in the container, and the inoculum in the cap, the combination may be stored indefinitely at ambient temperatures by the retailer.

The consumer may also store the product indefinitely. When the consumer is ready to use the product, he/she should first read the instructions on the bottle, to find the culture incubation conditions and time. Let us assume the culture incubation time is nominally 2 days at indoor room temperature. The consumer would then follow the directions on the bottle, 2 days before the culture is needed for dilution and use. The consumer then removes the cap from the bottle and sets it down. Then, the consumer opens the sterile pack containing the second cap or sealed plastic pipette with the inoculum contained therein and removes the seals to expose the inoculum. The cap or pipette containing the inoculum is placed in as on the container with the culture medium and the bottle is inverted several times to inoculate the medium. The consumer then places the culture in the appropriate location for growing the microorganisms with appropriate temperature controls between 25° C. and 30° C.

The invention may best be understood by reference to the following detailed description thereof, when taken in conjunction with the accompanying drawings in which:

DETAILED DESCRIPTION OF THE INVENTION

Figure 1:
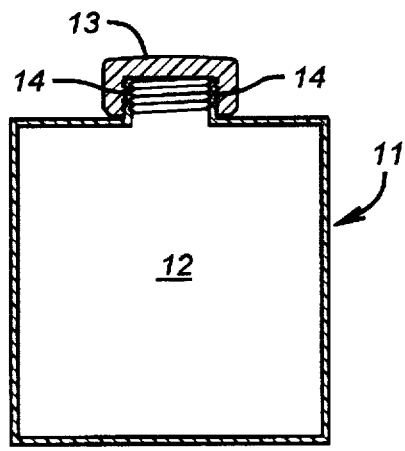
FIG. 1 is a schematic view in cross section showing a capped bottle of bacterial culture solution having an ordinary storage cap.

Referring initially to FIG. 1 a portion of the packaging system of the invention is shown is section. A bottle 11 containing a liquid culture solution 12 is packaged with a conventional cap 13 which affixes to the bottle 11 via threads 14.

The bottle 11 may be of any sterilizable material that will hold the sterile liquid broth medium 12 such as glass. The bottle 11 should be transparent and resistant to breaking and deformation. The bottle 11 can be of any size or shape as long as the shape is such that it is resistant to upsetting and overturning. The bottle 11 will be filled with liquid, so it could vary in size from a minimum of 150 ml (5.0 fl. oz.) to a maximum of 3.785 liters (1 gallon), for ease of use. When the use is for treating large agricultural tracts of land, larger containers of appropriate size should be used. Since the final product will normally be diluted by up to 1:50 with water, a nominal size of 500–1000 ml (17–39 fl. oz.) would be most convenient. These volumes will yield from 25–50 liters (6.6–13.2 gallons) of diluted, ready to use, microorganisms. The dilution rate will vary with the microorganisms and the media. The bottle may optionally contain a turbidity code of optimum growth (not shown) whereby the consumer may compare the turbidity of the microbial growth in the bottle to the code, which represents optimal turbidity. When the turbidity of the growth medium reaches the code, the culture is ready to use. The bottle 11 of composition as described above, is of standard construction, and is filled with sterile growth broth such as, LB broth as described in the copending application referenced above and covered with a standard screw on cap 13. The cap 13 on the bottle could have a standard safety plastic covering to prevent the cap from being loosened or removed until it is time to inoculate.

Figure 2:
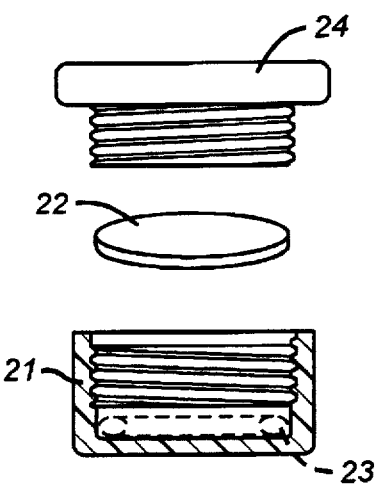
FIG. 2 is a schematic view in cross section showing a sterile packed second cap used in the system and a dummy plug therefor.
Figure 3:
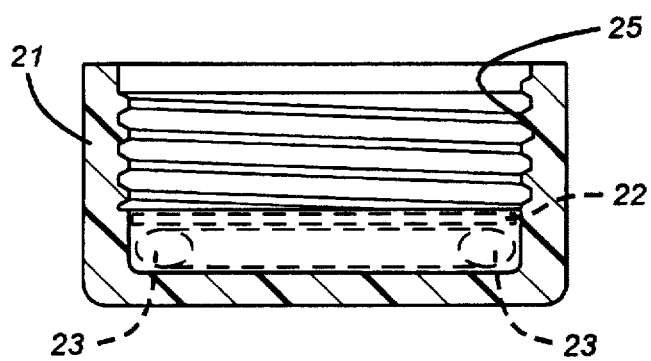
FIG. 3 is a larger schematic cross sectional showing in more detail the replaceable inoculant containing cap of the packaging system.

The inoculant storage cap 21 of FIG. 2 and 3 is completely sterile except for the inoculum and may be stored in a cold-sterilized, clear, impermeable, plastic bag or alternatively, a foil pack (not shown). The top inside of the storage cap contains an o-ring seat for a seal. A shim disc 22 made of metallic foil or plastic sits on the o-ring seat 23. The space subtended by the o-ring seal 23 shim disc 22 and the inside top of the cap 21 contains the inoculum. The volume of the space is about 1 cubic centimeter and holds about 1.0 ml of inoculum, but this volume may vary if desired. The inoculum will normally contain lyophilized microorganisms, but other types of preserved inocula are also applicable or even preferred in some instances. A threaded solid dummy plug 24 can be provided, if desired, for the storage cap 21. Use of the plug 24 can solidify and ruggalize the o-ring seal 23 and shim disc 22 for long term storage.

In operation the consumer then cuts open the bag containing the storage cap 21 and unscrews the solid threaded dummy plug 24. This exposes the foil or plastic shim disc 22 which covers the o-ring seal 23. The shim disc 22 is removed and discarded. This exposes the inoculum. The storage cap 21 containing the o-ring seal 23 and inoculum are then screwed onto the culture solution bottle 11 of FIG. 1. The bottle 11 is inverted gently to cause the growth medium 12 containing therein to wash the inoculum into the culture medium in the bottle. The culture medium is at this point inoculated and the incubation begins.

When the culture is turbid or has reached the coded turbidity, it is ready to dilute and use. The preferred diluent is well water without added disinfectants, but physiological saline solutions, buffer solutions, and 1% protein solutions, could all give excellent results. The user should note that using distilled water or water from a municipal water supply that has been treated with disinfectants or chemical flocculants as a diluent may adversely affect the results with some microorganisms.

The final concentration per unit volume of microorganisms produced by the culture conditions described will differ depending upon the following variables: (1) the microorganism grown, (2) the medium selected, (3) the incubation time, and (4) the incubation temperature. In most cases of incubation for 24–72 hours at room temperature in a complex medium such as LB broth, the maximum stationary phase culture can have from $1 \times 10^8$ to $5 \times 10^9$ microorganisms per ml, a dilution of 1:10 to 1:50 of culture broth. Up to this point the culture should contain only the inoculated microorganism, that is, it is monoxenic. If the diluent has not been previously sterilized and stored in a sterile container, the diluted culture will have a small number of contaminants, but not enough to adversely affect the results, particularly if the microorganism is Xenorhabdus, which has antibiotic characteristics. The consumer should be alerted to the fact that the unopened broth medium should be clear-not turbid. If there is any turbidity or sediment in the culture broth in the unopened bottle, this is an indication of contamination by undesired organisms.

Figure 4:
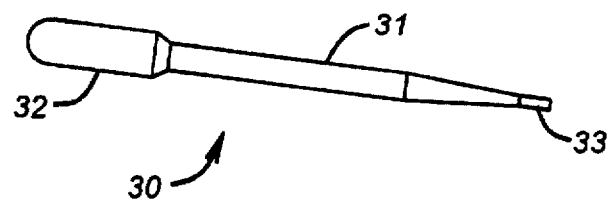
FIG. 4 is a schematic drawing showing a sterile sealed plastic pipette with the inoculum in an agar gel therein.

A second, alternative embodiment of a sterile packaging for the inoculant is shown in FIG. 4. A polyethylene pipette is shown generally at 30. The pipette has a one piece design which includes a barrel portion 31, a bulb portion 32 and a nozzle portion 33. Microbial inoculant may be grown on the LB broth medium previously described in liquid form or an agar gel. Either of these forms may be sucked up into the pipette 30 by compressing bulb 32 and immersing nozzle 33 in the inoculant. The one piece pipette 30 may then be sealed by heating and crushing together the nozzle tip portion 33, thus retaining sterilely packaged inoculant in the barrel portion 31 of the pipette 30. The sterile, inoculant containing pipette may then be packaged in a sterile plastic bag or envelope along with the bottle of culture solution 12 of FIG. 1. When it is desired to inoculate the culture solution 12, the cap 13 is removed, the tip of nozzle 33 of pipette 30 is snipped or cut off and the inoculant dropped into the culture solution 12 by squeezing the bulb portion 32 of the pipette 30. The pipette 30 may then simply be discarded.

The foregoing disclosures and descriptions may make other, alternative, embodiments of the invention apparent to those of skill in the art. The aim of the appended claims is to cover all such changes and modifications as fall within the true spirit and scope of the invention.

I claim:

1. A packaging system for use in packaging live microbial systems for an indefinite shelf life and for activating and conveniently culturing such microbial systems for use when desired, comprising:

a sealed sterile bottle capable of containing a liquid broth medium and having a first threadedly attached cap, said bottle being sized and shaped to be resistant to upsetting or overturning;

a liquid broth medium in said bottle, said broth being a sterile growth medium for a desired inoculant microorganism and;

a second, threadedly attachable storage cap, sized and adapted to replace said first cap, and being separately sterilely packed apart from said bottle, said second cap having an elastomeric o-ring seal disposed in the top thereof and an impermeable sealing disc sized to fill the diameter of said cap and to engage said o-ring seal forming a space between said seating disc and the top of said second cap and enclosed by said o-ring seal, for receiving a lypholized micro-organism inoculant and a solid threaded dummy plug adapted to be threadedly attached to said second cap, whereby upon removal of said dummy plug and said impermeable sealing disc and replacement on said bottle of said first cap with said second cap, said inoculant can be brought into intimate physical contact with said broth medium to thereby form an inoculated culture medium of said microorganism.

2. The system of claim 1 wherein said bottle comprises transparent glass.

3. The system of claim 2 wherein said second storage cap is separately packed sealed in sterile plastic.

4. The system of claim 2 wherein said second storage cap is separately packed sealed in sterile foil.

5. The system of claim 2 wherein said first and second caps comprise plastic caps.

6. The system of claim 5 wherein said elastomeric o-ring seal comprises a rubber o-ring seal.

* * * * *